US010493019B1

(12) United States Patent
Manenti

(10) Patent No.: US 10,493,019 B1
(45) Date of Patent: Dec. 3, 2019

(54) PERSONAL CARE OIL COMPOSITIONS

(71) Applicant: May 11, LLC, Brooklyn, NY (US)

(72) Inventor: Romina Manenti, Brooklyn, NY (US)

(73) Assignee: May 11, LLC, Brooklyn, NY (US)

( * ) Notice: Subject to any disclaimer, the term of this patent is extended or adjusted under 35 U.S.C. 154(b) by 0 days.

(21) Appl. No.: 16/124,411

(22) Filed: Sep. 7, 2018

Related U.S. Application Data

(60) Provisional application No. 62/555,446, filed on Sep. 7, 2017.

(51) Int. Cl.
*A61K 8/92* (2006.01)
*A61K 8/34* (2006.01)
*A61Q 5/00* (2006.01)

(52) U.S. Cl.
CPC .............. *A61K 8/922* (2013.01); *A61K 8/342* (2013.01); *A61K 8/347* (2013.01); *A61Q 5/002* (2013.01)

(58) Field of Classification Search
None
See application file for complete search history.

(56) References Cited

U.S. PATENT DOCUMENTS

| | | |
|---|---|---|
| 6,599,513 B2 | 7/2003 | Deckers et al. |
| 8,632,762 B2 | 1/2014 | Sargent |
| 9,066,952 B1 | 6/2015 | Brown |
| 9,415,082 B1 * | 8/2016 | Davis ..................... A61K 36/87 |
| 9,452,129 B1 | 9/2016 | Samuel et al. |
| 2003/0113391 A1 | 6/2003 | Brown et al. |
| 2008/0318833 A1 | 12/2008 | Jermann et al. |
| 2009/0068128 A1 | 3/2009 | Waddington |
| 2010/0063008 A1 * | 3/2010 | Matteliano ........... A61K 9/0014 514/159 |
| 2012/0237556 A1 | 9/2012 | Schlessinger et al. |
| 2016/0346339 A1 | 12/2016 | Finley et al. |
| 2016/0367473 A1 | 12/2016 | Kirakosyan |

FOREIGN PATENT DOCUMENTS

| | | |
|---|---|---|
| KR | 20170030739 A | 3/2017 |
| WO | 2017037534 A1 | 3/2017 |

OTHER PUBLICATIONS

Dias MFRG "Hair Cosmetics: An Overview" International Journal of Trichology Jan.-Mar. 2015, vol. 7, No. 1, pp. 2-15.
Trials N Tresses "10 Best Oils for Your Pre Poo." Retrieved from URL: <http://trialsntresses.com/natural-hair/10-best-oils-pre-poo>, Published online Feb. 9, 2015.
Sweet Essentials "100% Pure Organic Jamaican Black Castor Seed Oil Imported From Jamaica." Retrieved from URL: <https://www.sweetessentialsstore.com/products/100-pure-organic-jamaican-black-castor-seed-oil-imported-from-jamaica?variant=12998595078>, Dated Aug. 2, 2017.
The Herbarie "Optiphen." Retrieved from URL: <https://www.theherbarie.com/Optiphen.html>, Dated Aug. 2, 2017.
Pinterest "Explore Beauty tips, Hair Beauty, and More." Retrieved from URL: <https://www.theherbarie.com/Optiphen.html>, Dated Aug. 4, 2017.
Google Search Results for "unrefined Hemp Seed Oil Benefits." Retrieved from the Internet at URL: <https://www.google.com/search?rlz=1C1CAFB_enUS728US728&q=unrefined+hemp+seed+oil+benefits&sa=X&ved=0ahUKEwjTtpL3ucrVAhUI04MKH%E2%80%A6>, Dated Aug. 9, 2017.
Oilypedia "What is Black Castor Oil: A Miracle for Your Hair." Retrieved from the Internet at URL: <http://oilypedia.com/what-is-black-castor-oil-a-miracle-for-your-hair/>, Dated Aug. 4, 2017.
Priess R "Hair Cuticle 101—The Most Important Part of Your Hair." Retrieved from the Internet at URL: <https://www.howtomakeyourhairgrowfastertips.com/hair-cuticle-101-the-most-important-part-of-your-hair/>, Dated Sep. 9, 2018.
Wildly Natural Skin Care "Jamaican Black Castor Oil: What is it and Why Is It So Special" retrieved on Sep. 19, 2018. Retrieved from the Internet at URL: <https://www.wildly-natural-skin-care.com/jamaican-black-castor-oil.html>.
Fountain Pimento Oil "Jamaican Black Castor Oil Facts You Probably Didn't Know." Aug. 20, 2015. Retrieved from the Internet at URL: <https://www.fountainoil.com/blog/jamaican-black-castor-oil-facts-you-probably-didnt-know/>. castor-oil.com "Jamaican Black Castor Oil." Retrieved from the Internet at URL: <http://castor-oil.com/jamaican-black-castor-oil/>, Dated Sep. 19, 2018.
beautymunsta.com "7 Natural Oils That Penetrate the Hair Shaft." Retrieved from the Internet at URL: <http://beautymunsta.com/natural-oils-that-penetrate-the-hair-shaft/>, Dated Sep. 19, 2018.
Tadimalla RT "16 Benefits of Jamaican Black Castor Oil for Skin, Flair, and Health" StyleCraze Dec. 11, 2017. Retrieved from the Internet at URL: <https://www.stylecraze.com/articles/benefits-of-black-castor-oil/#gref>.

(Continued)

*Primary Examiner* — Jeffrey T. Palenik
(74) *Attorney, Agent, or Firm* — Maria Luisa Palmese; Thomas Woolf; Wuersch & Gering

(57) ABSTRACT

A new natural oil personal care composition and system for treating damaged hair and/or supporting healthy hair and healthy hair growth. The composition comprises a blend of natural oils including Jamaican black castor oil, and one or more of natural sweet almond oil (preferably unrefined), pure avocado oil, and hemp seed oil (preferably unrefined). The oils are preferably organic. The composition is useful for repairing damaged, depleted and/or thinning hair due to various factors, including inadequate nutrition or overproduction of sebum, which can result in hair loss. The composition is also useful for repairing dry, frizzy, oily, dull (low shine), and brittle hair that has been naturally damaged by the elements (e.g. the sun, heat, wind, and/or cold), by wearing head gear or hair accessories that create friction with the hair surface (e.g. helmets, hair elastics and hair bands), by inappropriate or overuse of hair styling tools (e.g. hair dryers, curling and straightening irons), and/or by chemical processes (e.g. hair dyes, perms, chemical straighteners, chemotherapies).

16 Claims, 13 Drawing Sheets

(56) References Cited

OTHER PUBLICATIONS

Sweet Essentials "100% Pure Organic Hemp Seed Oil | Unrefined / Virgin." Retrieved from the Internet at URL: <https://www.sweetessentialsstore.com/collections/pure-organic-beauty-oils/products/100-pure-organic-hemp-seed-oil-unrefined-virgin-imported-from-canada?variant=12592391238>, Dated Sep. 19, 2018.
Aromaweb "What are Carrier Oils." Retrieved from the Internet at URL: <https://www.aromaweb.com/articles/whatcarr.asp>, Dated Sep. 19, 2018.
Sweet Essentials "100% Pure Organic Sweet Almond Oil | Unrefined / Virgin." Retrieved from the Internet at URL: <https://www.sweetessentialsstore.com/collections/pure-organic-beauty-oils/products/100-pure-organic-sweet-almond-oil-unrefined-virgin-imported-from-italy?variant=12593022214>, Dated Sep. 19, 2018.
Reddit "Skincare Addiction—Basic Almond Oil Guide (Benefits, Uses, Science Inc)." Retrieved from the Internet at URL: <https://www.reddit.com/r/SkincareAddiction/comments/439k9v/research_basic_almond_oil_guide_benefits_uses/>, Dated Sep. 19, 2018.
Patterson S "12 Remarkable Benefits of Sweet Almond Oil for Beautiful Skin." Retrieved from the Internet at URL: <https://www.naturallivingideas.com/sweet-almond-oil-benefits/>, Dated Jun. 24, 2015.
Sweet Essential "100% Pure Organic Avocado Oil." Retrieved from the Internet at URL: <https://www.sweetessentialsstore.com/collections/pure-organic-beauty-oils/products/100-pure-organic-avocado-oil-imported-from-italy-1?variant=29995509068>, Dated Sep. 19, 2018.
Patterson S "12 Ways Using Hemp Seed Oil Will Improve Your Health & Your Life" Aug. 16, 2016. Retrieved from the Internet at URL: <https://www.naturallivingideas.com/hemp-seed-oil/>.
Silver Women "Romina Manenti." Retrieved from the Internet at URL: <https://thesilverwomen.com/may11-romina/>, Dated Sep. 19, 2018.
Cardellino C "This Is Exactly How to Get Runway-Worthy Hair" Nov. 28, 2017. Retrieved from the Internet at URL: <https://www.cosmopolitan.com/style-beauty/beauty/advice/g2415/how-to-get-victorias-secret-model-hair/?slide=8>.
Levinson L "Proof That the 2017 Victoria's Secret Fashion Show Is the Sexiest, Most Diverse Beauty Look Yet!" Dec. 2, 2017. Retrieved from the Internet at URL: <https://www.popsugar.com/beauty/photo-gallery/44228781/image/44276950/May-11-Hair-Oil>.

\* cited by examiner

PERSONAL CARE OIL COMPOSITIONS

CROSS REFERENCE TO RELATED APPLICATIONS

This application claims the benefit to U.S. Provisional Application No. 62/555,446 filed on Sep. 7, 2017, the entire contents of which are incorporated by reference.

BACKGROUND OF INVENTION

Hair is one of the defining characteristics of mammals. It is comprised of protein filaments that grow from hair follicles in the dermis, or skin. Except in areas of glabrous skin, the human body is covered in hair follicles that produce thick terminal or fine vellus hair. In humans terminal hair covers the head and is often considered one of the distinctive physical attributes of a person. Hair is also an important biomaterial and is primarily composed of protein, notably alpha-keratin.

Human and mammalian hair is subject to variety of stressors including aging, genetic predisposition, endocrine disorders, medication, nutritional factors, emotional stress, the natural elements, over-treatment with chemicals such as dyes, perms and straighteners, and physical stress (e.g. head coverings, hair braids and weaves). These stressors can result in hair loss or thinning, and in hair that is dry, frizzy, oily, brittle, damaged, dull and/or unmanageable. Hair loss or thinning is a common problem for both men and women, and provokes anxiety and distress that reflects the symbolic and psychosocial importance of hair. Hair loss can result from dry or brittle hair because, in this condition, hair breaks off close to the scalp or falls out from the follicle in excessive amounts. This type of abnormal hair loss is generally treated by attempting to keep the remaining hair supple and soft and encouraging new growth from the follicles in the scalp so as to prevent additional hair loss. Dandruff and excess sebum may also encourage hair loss. Dandruff is a common affliction usually associated with the human scalp area. The skin normally sloughs off skin surfaces, which are then washed away at frequent intervals so that the sloughing off process is not noticeable. Because the scalp is not normally washed as often as other parts of the body, the sloughed-off skin may accumulate on the scalp and together with the natural oils exuded by the scalp create a suitable environment for bacterial growth, some of which are known to be associated with hair loss. In addition, many hair products include ingredients that can contribute to hair loss, especially if the hair is fragile or previously damaged. For example, 90% of shampoos contain surfactants such as sodium lauryl sulfate that irritate the scalp and strip the hair of oils, making the hair weaker and more prone to damage. A vast majority of hair products also contain silicones. Silicone not only surrounds the hair, causing it to dry out from within, but also builds a non-water soluble layer on the scalp, causing sebum production to increase and build up under the silicone layer. Too much sebum results in an oily scalp, which in turn affects the hair growth cycle and can foster dandruff.

The market is replete with products promising to repair and restore damaged hair. However, these products are generally cosmetic; they treat only the surface look of the hair and do not repair or foster hair health by providing the hair with nutrients necessary to restore and maintain hair health.

Furthermore, although natural oils have been used for treating damaged hair, such compositions are generally not effective. Typically, they use one oil as a carrier and fail to provide the necessary nutrients to repair, protect and restore damaged hair and scalp. Furthermore, such compositions are generally difficult to use and often are not well-absorbed into the hair, rendering it heavy and dull and unpleasant to the touch. While lighter and faster absorbing hair oils can be used, they do not contain and therefore cannot provide the nutrition necessary to repair, protect and restore damaged hair and scalp. In fact, an oil product may be essentially completely absorbed by the hair but still not provide the desired beneficial effect on the hair because it does not have the hair nutrition components necessary to support healthy hair growth or repair damage hair.

Furthermore, many so-called natural oils on the market are not natural oils at all, because they include silicone oils as a primary ingredient. For example, KR20170030739A discloses a composition for hair care comprising silicone oils, natural vegetable oils, phenoxyethanol and Panthenol. While silicone oils may protect the hair strand against humidity and friction and initially appear to have a beneficial effect, they do not have any restorative properties for the hair and tend to dry out the hair in the long run. As discussed above silicones surround the hair, causing it to dry out from within. They also create a non-water soluble layer on the scalp, causing sebum production to increase and build up under the silicone layer. Silicones, especially water-insoluble ones, are difficult to wash out. Thus hair treated with products containing silicones requires aggressive shampoos to remove the silicone build-up from the hair and scalp, which further dries out the hair. In particular, water-insoluble silicones can be washed away only with shampoos containing sulfates. Furthermore, while the hair is coated with silicone, no other substance (e.g. oil, water, protein nutrients) can access the roots of the hair. Thus silicones also impede the absorption of nutritional ingredients included in the product. The presence of water-insoluble silicones in the hair therefore causes long-term damage to the hair resulting in drying and breakage. Ultimately straight or wavy hair tends to look greasy, heavy and dull.

There is therefore a need for a personal care oil composition that overcomes the above problems and is both well-absorbed and nourishing and effectively repairs, protects and fortifies hair.

SUMMARY OF INVENTION

The following summary is provided to further describe the invention and facilitate an understanding of some of the innovative features unique to the disclosed embodiments and is not intended to be a full description. A more comprehensive appreciation of the various aspects of the embodiments disclosed herein can be gained by taking the entire specification, claims, drawings, and abstract as a whole.

The present invention provides novel personal care oil compositions which include a novel blend of natural plant-based botanical oil extracts. Surprisingly, these compositions are both well-absorbed and nourishing and can be used to effectively repair, protect and fortify hair and to support healthy hair growth and regrowth by delivering vital hair nutrition. Furthermore, the composition of the present invention can be used universally i.e. on all hair types (curly, straight, wavy), textures (thickness of strands), densities (quantity of hair) and lengths, and low and high porosity hair, according to need and lifestyle. Another advantage of the present invention is that it is versatile and can be organically integrated into a user's life so that the full benefits, which require long term use, are obtained with little effort and without the need to create and maintain yet another routine. Because of this, the novel composition of the invention does not require sacrificing aesthetics or lifestyle, but rather empowers both. In fact use of the product integrates easily into a person's lifestyle in such a way as to allow hair to benefit over the long term as the user goes about his or her daily activities.

The composition of the present invention can be used effectively on both damp and dry hair, thereby eliminating the need for multiple products. It can be used as a pre-shampoo treatment to deeply restore the hair simply by applying the effective dosage for the hair type (including porosity and density) and leaving on the hair for a time period sufficient to allow effective absorption of the oils and thus delivery of their nutrients into the hair shaft. The composition can also be use post-shampoo to provide similar benefits over a longer period of time, or to extend the benefits of the pre-shampoo treatment. The post-shampoo application also serves to replenish oil lost due to overly aggressive shampoos. The composition may also be applied on dry hair to protect the hair from stressors, such as the elements or sports/workout activity, for example from contact with salt water, wind, sun and heat at the beach, or chlorine and other chemical agents in a swimming pool, or excessive sweat produced by sports activities, including for example hot yoga, or from friction with helmets used in work or sports activities, such as polo, fencing, bicycling or construction. The composition may also be applied to damp or dry hair to protect hair from styling tools and chemicals and to assist in the coloring process.

The personal care oil composition of the present invention is an essentially non-aqueous composition that comprises Jamaican black castor oil (JBCO), also known as black castor oil or *Ricinus communis* seed oil and one or more natural oils including sweet almond oil, avocado oil and hemp seed oil. The oils are preferably organic and can be refined or unrefined depending on the amount and type of impurities present. For example, unrefined sweet almond oil and unrefined hemp seed oil are preferred because the refining process eliminates essential nutrients. Other oils having similar physical and nutritive properties may also be used.

Preferably the personal care oil composition of the present invention comprises about 25 to 40% by volume Jamaican black castor oil, about 25 to 40% by volume organic sweet almond oil (preferably unrefined), about 15 to 30% by volume pure avocado oil in amounts, about 15 to 30% by volume hemp seed oil (preferably unrefined), about 0.5 to 2% by volume of a preservative (preferably an essentially paraben and formaldehyde free preservative) and optionally one or more fragrance oils. The amount of fragrance depends on the fragrance and could be from 5 to 10% by volume. For a lower viscosity product which may be more advantageous for finer hair, the amount of hemp seed oil may be lower, from about 10 to 15%. The amount of fragrance may also be lower for a product directed to individuals with allergies or sensitivities to fragrances, from about 2 to 5%.

The present invention also provides a method for stimulating hair growth; controlling hair thinning or loss; treating dry scalp or exfoliating the scalp; treating dry, brittle, frizzy, oily, chemically or physically damaged, and/or dull hair; and/or treating dandruff and infections resulting therefrom by topical application of the novel personal care oil composition described above.

The present invention also provides a kit for topical treatment of hair and/or skin of a mammal. The kit includes: a personal care oil composition described above, directions for application, a hair cap, and packaging material including a container for holding the personal care composition having a dropper, preferably a pump dropper, for application.

BRIEF DESCRIPTION OF THE DRAWINGS

The drawings are briefly described as follows.

DETAILED DESCRIPTION OF THE INVENTION

Figure 1:
FIG. 1 is a photograph of the subject of Example 4 showing hair prior to use of the composition of Example 1.

Unless specifically indicated otherwise, all technical and scientific terms used herein have the same meaning as commonly understood by those of ordinary skill in the art to which this invention belongs. In addition, any method or composition similar or equivalent to a method or composition described herein can be used in the practice of the present invention. The following terms shall have the meanings stated therewith.

As used herein, the term "natural personal care oils" refers to oils derived by solvent extracting or mechanical pressing of plant flowers, leaves, bark, stems, roots, and/or seeds that are known to be generally safe for use in formulations intended for topical application to mammals, in particularly humans.

As used herein, the term "about" refers to a variation of 10 percent of the value specified; for example about 50 percent carries a variation from 45 to 55 percent.

As used herein, the term "and/or" refers to any one of the items, any combination of the items, or all of the items with which this term is associated.

As used herein, the singular forms "a," "an," and "the" include plural reference unless the context clearly dictates otherwise. It is further noted that the claims may be drafted to exclude any optional element.

As used herein, the term "administration" refers to a method of placing a composition or formulation in a desired site.

As used herein, the terms "include," "for example," "such as," and the like are used illustratively and are not intended to limit the present invention.

As used herein, the term "mammal" refers to a warm blooded animal, preferably a domesticated animal or human subject.

As used herein, the term "topically" refers to application of the compositions of the present invention to the surface of the skin, scalp, and hair follicle, keratin, and cuticles including facial hair.

As used herein, the term "natural" with respect to oils refers to plant-based extract botanical oils derived from botanical plants that contain no artificial flavor or flavoring, coloring ingredient, or chemical preservative.

As used herein, the term "unrefined" refers to plant-based extracts of botanical oils that are not processed to remove impurities or unwanted elements.

Plant-Based Extract Botanical Oils

Jamaican Black Castor Oil (JBCO).

Jamaican black castor oil is also known as black castor oil or by its INCI name, *Ricinus communis* seed oil it is considered to be an all-purpose personal care healing oil, commonly used for hair and scalp problems (see U.S. Pat. No. 9,066,952 B1) in the Caribbean. The oil is said to seal moisture in the hair with a protective coat. Jamaican black castor oil is rich in the fatty acid triglyceride ricinoleic acid which is thought to be responsible for its healing abilities. Ricinoleic acid is an effective topical treatment for pruritus (itching) of the scalp. Ricinoleic acid also possesses analgesic and anti-inflammatory activity and is thought to increase blood flow to where it is applied. Ricinoleic acid is also said to help balance scalp pH, which can also help replenish the scalp's natural oils and undo some of the damage of harsh chemical hair products (and even damage from no-poo shampoo, due to over alkalinity). The antioxidants in Jamaican black castor oil are also said to support the keratin in hair and to aid in making hair stronger, smoother and less frizzy.

Castor oil, like all vegetable oils, has different physical and chemical properties depending on the method of extraction. Most of Jamaican black castor oil's benefits over yellow castor oil originate from the process of roasting. Roasting the castor beans prior to extraction makes the final product "ashier". This ash increases the alkalinity of the Jamaican black castor oil over yellow castor oil. Increased alkalinity raises the cuticle layer (protective layer of the hair) which allows the hair to receive the moisture and nutrients it needs from the oil to increase hair thickness. The higher pH can help to clarify the scalp and remove anything that may be clogging hair pores.

Jamaican black castor oil is made by first roasting castor seeds obtained from the plant *Ricinus communis*. The roasted seeds are pulverized and extracted into boiling water. The oil-water mixture is allowed to cool and the black oil separates to the top and is collected. The roasting produces the black color and a richer, earthier aroma. The finished product is a pure, unadulterated, thick, pungent, dark brown oil, hence the name Jamaican black castor oil. If the castor oil is too dark, it has been over-roasted and is burnt. Burnt castor oil is irritating and should be avoided.

Jamaican black castor oil has been used by Caribbean women to moisturize, thicken, strengthen and rapidly increase hair growth. It is said to increase blood flow to the scalp, supplying valuable nutrients to hair follicles, and prevent hair breakages, dandruff, eczema and dry, itchy scalp. Jamaican black castor oil has crossed over into other ethnic groups, and is now being used more widely for some of the same purposes, as well as new found uses including eyelash and eyebrow hair growth and as a massage oil.

Jamaican black castor oil, however, suffers from the disadvantage that it is unpleasant and inconvenient to use. For example, it cannot be used on dry (not wet or damp) hair without compromising aesthetics and lifestyle. It is thick and highly viscous, and when applied directly to the hair or scalp has a tacky sticky feel. It also has an intense nutty, smokey odor which may be perceived as highly unpleasant and even nauseating. Treatment with Jamaican black castor oil generally involves applying the oil directly to the hair for an overnight treatment with the need for a hair cap. Following overnight application, residual oil on the hair and scalp is removed by washing with shampoos. Because of its viscosity and tackiness, removing the oil often requires more than one shampoo in order to achieve a clean hair surface. The need for multiple shampoos often decreases or entirely eliminates the benefit of the treatment due to stripping of oils from the hair and overwashing.

Organic Sweet Almond Oil.

Sweet almond oil is considered a nutrient for skin conditioning comprising glucosides, vitamins, and minerals, and said to aid with eczema and itchy, dry, and inflamed skin (see U.S. Pat. No. 9,415,082 B1). Sweet almond oil is said to nourish hair and sooth hair cuticles, making the user's hair longer and thicker, adding shine to the hair, and controlling hair loss. Unrefined sweet almond oil is preferred in the composition of the present invention in order to provide maximum nutrition.

Avocado Oil, also known under its INCI name, *Persea gratissima* oil, is pressed from the fleshy pulp of the fruit of the avocado tree *Persea americana*, and is said to have lubricating, regenerative, and moisturizing properties (see U.S. Pat. No. 9,066,952 B1). Avocado oil is thick in consistency with excellent penetration enhancer properties. It is also rich in fatty acids such as oleic and linoleic and contains powerful antioxidants that are useful for healing damaged hair from heat tools/UV rays. Preferably the avocado oil used in the composition of the present invention is pure avocado oil. Unrefined pure avocado oil may also be used in the composition of the present invention.

Hemp Seed Oil.

Hemp seed oil, also known as *cannabis* seed oil, is a natural oil that can be obtained by cold pressing hemp seeds, which are seeds from the plant species *Cannabis sativa* (see U.S. Pat. No. 9,415,082 B1 and KR20170030739A). Hemp seed oil contains high amounts of omega-3 and omega-6 poly-unsaturated essential fatty acids as compared to other plant-based botanical oils. Hemp seed oil also contains antioxidants in the form of vitamin E acetate and carotene. Hemp seed oil is said to have anti-inflammatory and antioxidant properties and is high in essential fatty acids. Hemp seed oil is said to be non-greasy and a good source of many nutrients that can benefit hair health. It is said to be helpful for developing keratin formation. Topical application of hemp seed oil is said to help to develop stronger and healthier hair and can be used with oily, dry, damaged or normal hair. Preferably the Hemp seed oil used in the composition of the present invention is unrefined.

In addition to the natural oils, the formulation comprises an effective amount of an added preservative, preferably an essentially paraben and formaldehyde free preservative that is compatible with an essentially non-aqueous oil blend. A preferred preservative is phenoxyethanol in a caprylyl glycol emollient base (Optiphen®). The composition may optionally include one or more fragrance oils compatible with essentially non-aqueous oil blend, preferably synthetic fragrance oils.

Compositions

The present essentially non-aqueous personal care oil compositions are comprised of natural plant-based extract botanical oils including Jamaican black castor oil, sweet almond oil, pure avocado oil, hemp seed oil, and one or more preservatives essentially free of parabens and formaldehyde. The personal care oil compositions may optionally contain one or more fragrance oils. The plant-based extract botanical oils are preferably obtained from organic sources and may be refined or unrefined. The sweet almond oil and hemp seed oil are preferably unrefined so as to provide a broader nutrient profile.

Preferably, the personal care oil composition of the present invention comprises up to about 40% by volume Jamaican black castor oil, up to about 40% by volume organic sweet almond oil (preferably unrefined), up to about 30% by volume pure avocado oil, up to about 30% by volume hemp seed oil essentially paraben and formaldehyde free preservative) and optionally one or more fragrance oils. The amount of fragrance depends on the fragrance and could be up to 10% by volume.

Preferably, the personal care oil composition of the present invention comprises about 25 to 40% by volume Jamaican black castor oil, about 25 to 40% by volume organic sweet almond oil (preferably unrefined), about 15 to 30% by volume pure avocado oil, about 15 to 30% by volume hemp seed oil (preferably unrefined), about 0.5 to 2% by volume of a preservative (preferably a essentially paraben and formaldehyde free preservative) and optionally one or more fragrance oils. The amount of fragrance depends on the fragrance and could be from 5 to 10% by volume. This composition may be varied somewhat. For example, for a composition which is lower in viscosity and more easily penetrates the hair, especially fine hair, the amount of hempseed oil may be lowered, e.g. to about 5-10%; for a composition that is directed to people with fragrance sensitivities, a fragrance may be omitted altogether or added in very low quantities, e.g. about 2-5%.

More preferably the personal care oil composition of the present invention comprises about 30 to 35% by volume Jamaican black castor oil, about 30 to 35% by volume organic sweet almond oil (preferably unrefined), about 20 to 25% by volume pure avocado oil, about 20 to 25% by volume hemp seed oil (preferably unrefined), about 0.5 to 1% by volume of a preservative (preferably a essentially paraben and formaldehyde free preservative) and optionally one or more fragrance oils. The amount of fragrance depends on the fragrance and could range up to 10% by volume.

More preferably the personal care oil composition of the present invention comprises by volume about 29-30% Jamaican black castor oil, about 27-28% unrefined organic sweet almond oil, about 19-20% pure avocado oil in, about 15-16% unrefined hemp seed oil, about 1% essentially paraben and formaldehyde free preservative, and optionally one or more natural fragrance oils in an amounts of about 7-8%.

Another preferable embodiment of the personal care oil composition of the present invention comprises by volume about 28-34% Jamaican black castor oil, about 28-34% unrefined organic sweet almond oil, about 19-23% pure avocado oil in, about 11-14% unrefined hemp seed oil, about 0.90-1.1% essentially paraben and formaldehyde free preservative, and optionally one or more natural fragrance oils in an amounts of about 3-5%. A lower percentage of hemp seed oil produces a personal care oil composition that is lower in viscosity with an improved application to hair, especially to fine hair. Additionally, a lower viscosity personal care oil composition allows improved penetration and/or absorption into hair of nutrients from the organic oils.

The essentially non-aqueous personal care oil composition is prepared by addition of natural plant-based extract botanical oils based on individual boiling points with the highest boiling point natural plant-based extract botanical oil Jamaican black castor oil added first followed by pure avocado oil, unrefined organic sweet almond oil, and unrefined hemp seed oil.

Preferably, the composition of the invention is prepared by adding the Jamaican black castor oil to a mixing vessel and heating and stirring the oil at a range of about 150° F. to about 200° F. for about 30-40 minutes to minimize the amount of sediments in the oil, thus obtaining a uniform composition. The temperature of the Jamaican black castor oil is then reduced to about 180° F. and the pure avocado oil is added. The resultant oil composition is heated with stirring at about 180° F. for about 30-40 minutes to form a homogenous oil composition. The temperature of this resultant oil composition is reduced to about 160° F., the unrefined organic sweet almond oil is added, and the resultant oil composition is heated with stirring at about 160° F. for about 30-40 minutes to form a homogenous oil composition. The temperature of the resultant homogenous oil composition is then further reduced to about 130° F. and the unrefined hemp seed oil is added. The resultant oil composition is heated with stirring at about 130° F. for about 30-40 minutes to form a homogenous combined oil composition comprised of the four natural plant-based extract botanical oils. This homogenous combined oil composition is then heated to about 130° F. and the one or more essentially paraben and formaldehyde-free preservatives are added. After a period of time sufficient to allow the preservative(s) to exert its antimicrobial effect, one or more fragrance oils are optionally added at about 130° F. If a mixture of fragrance oils are added, the selected fragrance oils are preferably mixed together to form a fragrance oil blend and stored for at least two weeks prior to addition of the one or more fragrance oil.

The final composition should have a pH greater than about 6 and preferably about 6 to about 6.5.

The finished composition may be stored at room temperature in any suitable container, but is preferably stored in the dark. Preferably the composition is packaged in a glass container fitted with a dropper containing cap. The dropper is preferably a pump dropper.

Method of Use

The invention provides a method for promoting hair growth; repairing damaged hair and/or maintaining healthy hair. Preferably, the composition is applied by placing the desired amount in the palm of the hand, rubbing it between the palms. The hands are then placed in the roots of the hair and the oil is massaged into the hair with a circular motion extending the oil through the lengths of the hair. The hands are pressed into the hair in a consistent way until there is essentially no remaining oil on the palms of the hand.

In one embodiment, the method of treating hair comprises applying the composition of the invention to post-shampoo damp hair. The amount to be applied may vary from about 1 to about 12 drops of a standard cosmetic/medicinal dropper (about 0.02 to about 0.05 mL/drop, preferably 0.03 mL/drop) depending on the type and length of hair. For example, an application of 2-4 drops is generally suitable for fine hair, 4-6 drops is generally suitable for medium hair, and 6-8 drops is generally suitable for thick hair. For shoulder length or longer hair, an additional 2-4 drops may be necessary. Preferably, the composition is applied by rubbing the desired amount between the palms of the hand, placing the hands onto the hair roots, and massaging the hair roots in a circular motion and spreading the composition throughout the length of hair by pressing the hair consistently until there is little to no remaining oil on the palms of hand.

In another embodiment the composition of the invention is applied to dry hair for overnight pre-shampoo treatment. Preferably, ten drops of the composition are applied to dry hair by rubbing the composition between the palms of the hand, placing the hands onto the hair roots and massaging the hair roots in a circular motion. Following this application, an additional ten drops are applied to the hair and combed throughout the rest of the hair. Optionally in the case of long hair, the hair is secured in a loose bun. The composition is left in the hair for a minimum of six hours and preferably overnight or until lifestyle requires cleaner hair. Afterwards the hair is washed with a gentle shampoo. The amount of composition used may vary depending on the hair, but should be enough to coat the hair.

In another embodiment, the method comprises treating hair prior to physical exercise in order to protect the hair during workouts. Preferably about 1 to 15 drops of a standard cosmetic/medicinal dropper (about 0.02-0.05 mL/drop, preferably 0.03 mL/drop) of the essentially non-aqueous novel personal care oil composition are applied by rubbing the desired amount of the composition between the palms of the hand, placing the hands onto the hair roots, and massaging the hair roots in a circular motion and spreading the essentially non-aqueous novel personal care oil composition throughout the length of hair by pressing consistently until there is little to no remaining oil on the palms of hand. The amount of composition used may vary depending on the hair, but should be enough to coat the hair. Following physical exercise the hair can be washed with a gentle shampoo to remove excess oil. Optionally the oil may be left in for overnight treatment.

In another embodiment, the method comprises daily treatment as a pick-me up or to restore dry ends. One to three drops of the composition (about 0.02-0.05 mL/drop, preferably 0.03 mL/drop) are rubbed between the palms of the hand and then applied to the ends of the hair.

In another embodiment, the method comprises using the composition before and/or after styling to protect hair before contact with the damagingly high temperature of hair styling tools and/or enhance hair shine after styling. Three to five drops of the composition (about 0.02-0.05 mL/drop, preferably 0.03 mL/drop) are rubbed between the palms of the hand and then applied to the hair prior to or after styling by using fingertips to making medium-sized separations starting from the back of the hair from the length to the ends, distributing the oil vertically on the hair separation from back to front by pressing the oil into the hair. The oil will define and bring an extra luminous effect into the hair, creating natural hair separations, and giving more natural movement to the hair.

In another embodiment, the method comprises using the composition before coloring to protect hair and assist in the coloring process.

Kits

The present invention also provides a kit for topically treatment of hair and/or skin of a mammal. The kit includes: a personal care oil composition of the present invention; directions for application, a hair cap, and packaging material including a container for holding the personal care composition and a dropper for application. The dropper is preferably a pump dropper.

The invention is now further illustrated with the following non-limiting examples, in which the natural plant extract oils, fragrance oils, and preservatives were obtained from commercial sources.

EXAMPLES

Example 1

Preparation of Personal Care Composition

Approximately 320 mL of Jamaican black castor oil is added to a 1 Liter vessel and heated with mixing for about 30 minutes to achieve a temperature of about 200° F. and a uniform oil composition. The temperature is reduced to about 180° F. Approximately 210 mL of pure avocado oil is added to the oil composition followed by heating and mixing for about 30 minutes to achieve a temperature of about 180° F. The combined oil composition is reduced in temperature to about 150° F. to 160° F. and about 300 mL of unrefined natural sweet almond oil is added to the combined oil composition followed by heating and mixing for about 30 minutes to achieve a temperature of about 150° F. to 160° F. The combined oil composition is reduced in temperature to about 130° F. and about 170 mL of unrefined hemp seed oil is added to the combined oil composition followed by heating and mixing for about 30 minutes to achieve a temperature of about 130° F.

The resultant combined oil composition is homogenous in appearance and the temperature is reduced to about 130° F. To the 130° F. homogenous combined oil composition is added 8 mL of paraben and formaldehyde-free preservative, preferably phenoxythanol in a caprylyl glycol emollient base (optiphene) and resultant combined homogenous oil composition is mixed for 30 minutes. Finally, a prepared blend of fragrance oils is added to the combined homogenous oil composition and the composition is mixed for about 30 minutes. Prior to addition, selected fragrance oils are mixed together to form a fragrance oil blend and stored for at least two weeks.

The resulting personal care composition has a pH of about 6.2.

TABLE 1

Personal care composition

| Ingredients | ml/Percentage of total composition |
|---|---|
| Jamaican black castor oil | 320 mL |
| Pure avocado oil | 210 mL |
| Unrefined organic sweet almond oil | 300 mL |
| Unrefined hemp seed oil | 170 mL |
| phenoxythanol in a caprylyl glycol emollient base (optiphen ®) | 0.8% based on 1000 mL |
| Synthetic Fragrance oils | 8% based on 1000 mL |

Example 2

Preparation of a Lower Viscosity Personal Care Composition

Approximately 325 mL of Jamaican black castor oil is added to a 1 Liter vessel and heated with mixing for about 40 minutes to achieve a temperature of about 200° F. and a uniform oil composition. The temperature is reduced to 180° F. Approximately 220 mL of pure avocado oil is added to the oil composition followed by heating and mixing for about 40 minutes to achieve a temperature of about 180° F. The combined oil composition is reduced in temperature to about 160° F. and about 325 mL of unrefined natural sweet almond oil is added to the combined oil composition followed by heating and mixing for about 40 minutes to achieve a temperature of about 160° F. The combined oil composition is reduced in temperature to about 130° F. and about 130 mL of unrefined hemp seed oil is added to the combined oil composition followed by heating and mixing for about 40 minutes to achieve a temperature of about 130° F.

The resultant combined oil composition is homogenous in appearance and the temperature is reduced to about 130° F. To the about 130° F. homogenous combined oil composition is added about 10 mL of paraben and formaldehyde-free preservative, preferably phenoxythanol in a caprylyl glycol emollient base (Optiphen®) and resultant combined homogenous oil composition is mixed for about 30 minutes. Finally, about 40 mL of a prepared blend of fragrance oils is added to the combined homogenous oil composition and the composition is mixed for about 30 minutes. Prior to addition, selected fragrance oils are mixed together to form a fragrance oil blend and stored for at least two weeks.

The resulting personal care composition has decreased viscosity, decreased stickiness, improved tactile feel, and improved application especially for finer hair, as well as the composition is easier to more evenly distribute on hair as compared to the composition of Example 1. In addition, the lower percentage of fragrance oils is particularly advantageous to individuals who have sensitivity or allergies to fragrances.

TABLE 2

Personal care composition

| Ingredients | ml/Percentage of total composition |
|---|---|
| Jamaican black castor oil | 325 mL |
| Pure avocado oil | 220 mL |
| Unrefined organic sweet almond oil | 325 mL |
| Unrefined hemp seed oil | 130 mL |
| phenoxythanol in a caprylyl glycol emollient base (optiphen ®) | 1.0% based on 1000 mL |
| Synthetic Fragrance oils | 4.0% based on 1000 mL |

Example 3

Method of Treating Hair

The personal care compositions of Examples 1 and/or 2 are applied topically to the hair of a human subject in amounts shown in Table 3. The personal care oil composition is rubbed between the palms of the hand followed by placing the hands onto the roots of the hair touching the scalp. The roots are massaged in a circular motion. The oil is then extended throughout the lengths of hair by pressing consistently until there is little to no remaining oil on the palms of hand. At this point, the hair has absorbed the desired quantity of oil it needs.

For Pre-Shampoo/Overnight Treatment the personal care compositions of Examples 1 and/or 2 are applied on dry hair, left in for at least 6 hours, followed by shampoo. With treatment twice a week results are obtained in 8 months and improvement is visible in four months. Sufficient oil must be applied to coat the hair. The preferred dosage amount is about 20 drops of a standard dropper (about 0.02-0.05 mL/drop, preferably 0.03 mL/drop). 10 drops are applied first and massaged into the roots and the remaining 10 drops are applied to the rest of the hair by pressing the hands on the hair, massaging and combing the oil throughout the length. Long hair is preferably secured in a loose bun. Preferably the composition is left on overnight and washed with a gentle shampoo in the morning to eliminate leftover oil. More or less of the composition may be used depending on the hair type and length of hair.

For Post Shampoo Treatment, the personal care compositions of Examples 1 and/or 2 are applied on clean damp hair in the amount recommended in Table 3 and the hair is styled as desired. With treatment two to three times a week, every time hair is washed, results are obtained in eight months and improvements visible in four months.

For Workout Treatment, the personal care compositions of Examples 1 and/or 2 are applied on dry or damp hair before workout. Sufficient oil must be applied to coat the hair. The preferred dosage amount is about 10 to 20 drops of a standard dropper (about 0.02-0.05 mL/drop, preferably 0.03 mL/drop). This treatment helps protect hair health and luster from the damaging effect of heat, extreme outdoor conditions and the acidity of sweat. After the workout, the hair may be washed with a gentle shampoo or left in for a longer treatment if a person's schedule permits.

For Daily Treatment, the amount in Table 3 is applied to the fingertips and then pressed on to the roots of the hair.

For Before and After Styling to protect hair from damaging high temperature hair tools such as curling irons, straightening irons etc., the amount in Table 3 is applied, preferably before and after styling. Preferably on dry hair apply the oil with fingers tips, taking medium separations start from the back of the hair from the length to the ends, and distributing the oil on vertical hair separation from back to front, and pressing the oil into the hair. The oil will define and bring an extra luminous effect into the hair and create a natural hair separation, giving more natural movement and softening the shape.

Before coloring to protect hair and assist in the coloring process the amount in Table 3 may be applied as described above. The oil may be applied directly to the hair to be colored, or added to the hair color mixture.

TABLE 3

Amount of Personal Care Oil Composition Added to Human Hair for Post Shampoo or Before/After Styling or Coloring

| Hair Type | Amount of personal care oil composition |
|---|---|
| Fine Hair | 2-4 drops* |
| Medium Hair | 4-6 drops |
| Thick Hair | 6-8 drops |
| Hair lengths below the shoulder | Add 2-4 extra drops |

*about 0.02-0.05 mL/drop, preferably 0.03 mL/drop

Example 4

Female Subject Using Composition of the Invention

Before use subject's hair was unpredictable. It could be very frizzy in between washes and a lot of product was necessary to combat frizz and manage curls. Curls were also losing definition and volume. Subject was losing a lot of hair in every wash and hairline looked like it was receding. Hair was patchy. Subject was very self-conscious about hairline and even tried products to help treat hairline. She tried one which required nightly application, but it did not work. Subject began using the composition of the invention as follows:

Overnight treatment twice weekly
Workout treatment once weekly
After shampoo treatment twice weekly (after every shampoo) Subject began treatment with the composition of Example 1 for 17 months and switched to the composition of Example 2 for the next two months.

Figure 2:
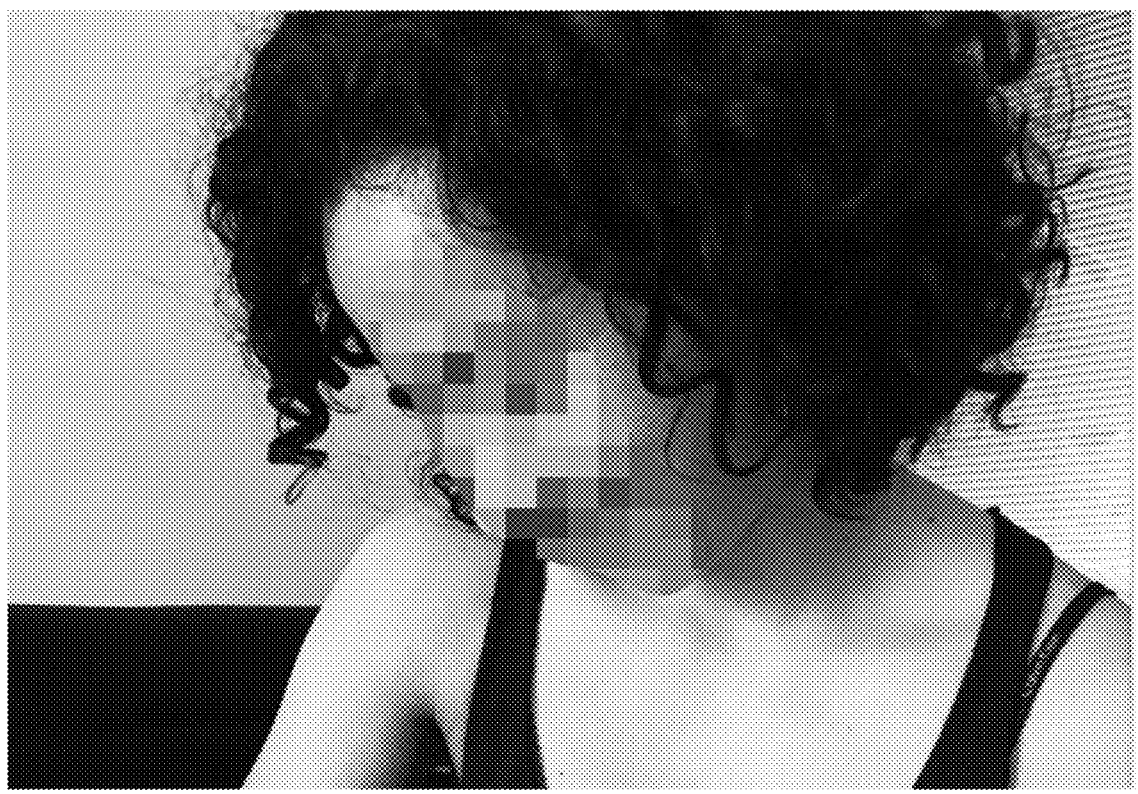
FIG. 2 is another view of photograph of the subject of Example 4 showing hair prior to use of the composition of Example 1.
Figure 3:
FIG. 3 is a photograph of the same subject showing hair after four months of using the composition of Example 1.
Figure 4:
FIG. 4 is a photograph of the same subject showing hair after nine months of using the composition of Example 1.
Figure 5:
FIG. 5 is a photograph of the same subject showing hair after ten months of using the composition of Example 1.
Figure 6:
FIG. 6 is a photograph of the same subject showing hair after seventeen months of using the composition of Example 1.
Figure 7:
FIG. 7 is a photograph of the same subject showing hair after nineteen months of using the composition of Example 1 for the first seventeen months and the composition of Example 2 for the last two months.

Subject started seeing hair improvement after a few months. Less hair fell out during washes and hair started feeling robust again. After twelve months hair was frizzy and had more definition, with considerably less hair loss between washes. Subject can wash hair less frequently and hairline is improving, with baby hairs around hairline growing longer and stronger. Subject notices more shine and bounce in curls and uses less styling products. Hair is much easier to detangle and feels full again. Results are shown in FIGS. 1-7.

Example 5

Male Subject Using Composition of the Invention

Before using composition of Example 1, hair was a little patchy in sections and subject felt the need to cut it quite short to reduce the appearance of the patchy sections. Subject also had a lot of dandruff and was washing hair twice a day with anti-dandruff shampoo. Subject was worried that hairline was receding. Subject could not wear hair longer because it would be unruly and hard to manage. Hair also appeared flat and dull.

Subject began using the composition of Example 1 as follows:

Overnight treatment three times weekly
After shampoo treatment daily (after every shampoo) Subject began treatment with the composition of Example 1 for the first 17 months and switched to the composition of Example 2 for the next two months.

Figure 8:
FIG. 8 is a photograph of the subject of Example 5 showing hair prior to use of the composition of Example 1.
Figure 9:
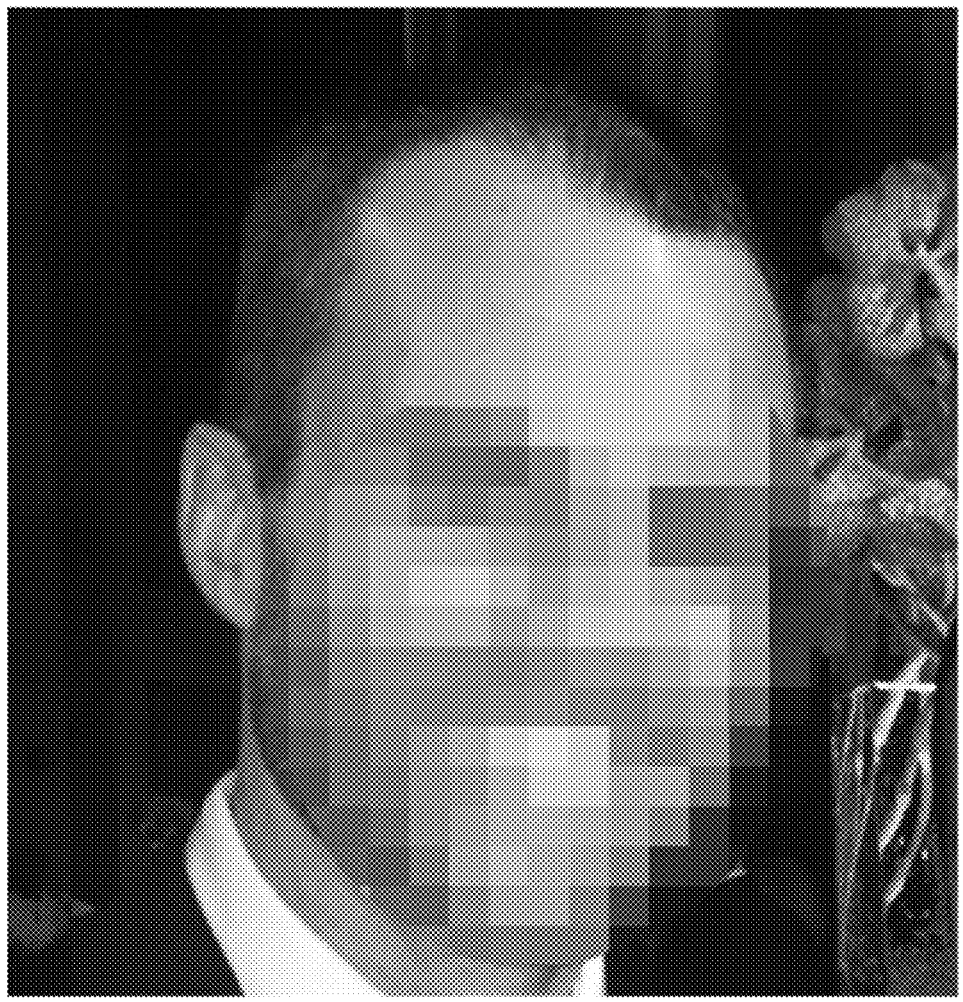
FIG. 9 is a photograph of the subject of Example 5 showing hair after one month of use of the composition of Example 1
Figure 10:
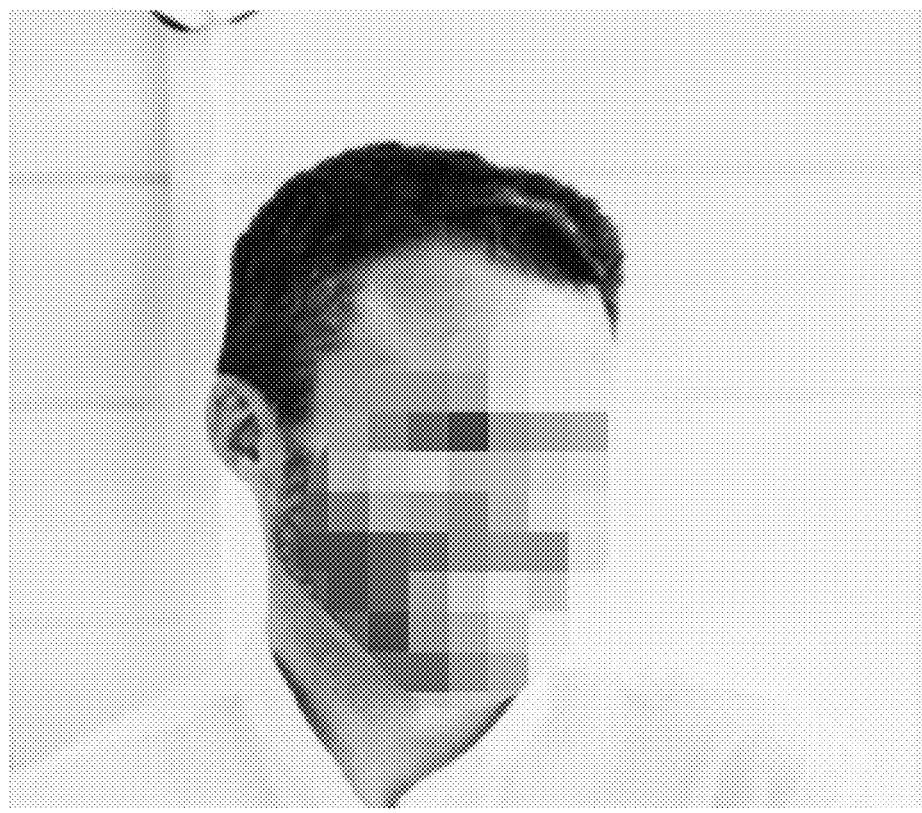
FIG. 10 is a photograph of the subject of Example 5 showing hair after four months of using the composition of Example 1.
Figure 11:
FIG. 11 is a photograph of the subject of Example 5 showing hair after six months of using the composition of Example 1.
Figure 12:
FIG. 12 is a photograph of the subject of Example 5 showing hair after nineteen months of using the composition of Example 1 for the first seventeen months and the composition of Example 2 for the last two months.
Figure 13:
FIG. 13 is another photograph of the subject of Example 5 showing hair after nineteen months of using the composition of Example 1 for the first seventeen months and the composition of Example 2 for the last two months.

After eight months subject saw improvement in hairline and fuller hair all over head with little or no dandruff. Subject no longer uses anti-dandruff shampoo. Subject began washing hair less often. After about four months subject and started to shampoo only once a day. Subject now feels comfortable wearing hair longer and notices more shine to hair. Results are illustrated in FIGS. 8-13.

I claim:

1. A personal care composition comprising about 25% to about 40% by volume of Jamaican black castor oil, about 25% to about 40% by volume organic sweet almond oil, about 15% to about 30% by volume pure avocado oil, about 10% to about 30% by volume hemp seed oil, a preservative comprising phenoxyethanol in a caprylyl glycol emollient base, and optionally, one or more fragrance oils.

2. The personal care composition of claim 1, wherein the sweet almond oil is unrefined sweet almond oil.

3. The personal care composition of claim 1, wherein said composition is a hair oil composition.

4. The personal care oil composition of claim 3 wherein the hemp seed oil comprises about 15% to 30% by volume.

5. The personal care oil composition of claim 1 wherein the hemp seed oil is unrefined hemp seed oil.

6. The personal care composition of claim 1, wherein the preservative is present in an amount of about 0.5% to about 2% by volume of the composition.

7. The personal care oil composition of claim 6 wherein the organic sweet almond oil is unrefined sweet almond oil.

8. The personal care oil composition of claim 1 wherein the personal care composition comprises about 28% to 34% by volume Jamaican black castor oil, about 28% to 34% by volume organic sweet almond oil, about 19% to 23% by volume pure avocado oil, and about 11% to 14% by volume hemp seed oil, about 0.5% to 2% by volume of an essentially paraben and formaldehyde free preservative, and optionally one or more fragrance oils.

9. The personal care oil composition of claim 8 wherein the organic sweet almond oil is unrefined sweet almond oil.

10. The personal care oil composition of claim 8 wherein the hemp seed oil is unrefined hemp seed oil.

11. The personal care oil composition of claim 8 wherein the essentially paraben and formaldehyde free preservative is phenoxyethanol in a caprylyl glycol emollient base.

12. The personal care composition of claim 8, wherein said composition is a hair oil composition.

13. A process for manufacturing a personal care composition comprising:
   (a) heating and stirring Jamaican black castor oil in a vessel until the oil reaches about 200° F. and maintaining the heating and stirring for about 40 minutes;
   (b) reducing the temperature of the Jamaican black castor to about 180° F. and then adding pure avocado oil to the Jamaican black castor oil;
   (c) heating and stirring the combined oils at about 180° F. for about 40 minutes to produce a homogenous composition of Jamaican black castor oil and pure avocado oil
   (d) reducing the temperature of the homogenous composition of Jamaican black castor oil and pure avocado oil obtained in step (c) to about 160° F. and then adding unrefined organic sweet almond oil to the homogenous composition of step (c);

(e) heating and stirring the mixture of Jamaican black castor oil, pure avocado oil and unrefined organic sweet almond oil obtained in step (d) at about 160° F. for about 40 minutes to produce a homogenous composition of Jamaican black castor oil, pure avocado oil and unrefined organic sweet almond oil;

(f) reducing the temperature of the homogenous composition of Jamaican black castor oil, pure avocado oil and unrefined organic sweet almond oil obtained in step (e) to about 130° F. and then adding unrefined hemp seed oil to the homogeneous composition of step (e);

(g) heating and stirring the mixture of Jamaican black castor oil, pure avocado oil, unrefined organic sweet almond oil, and unrefined hemp seed oil of step (f) at about 130° F. for about 40 minutes to produce a homogenous composition of Jamaican black castor oil, pure avocado oil, unrefined organic sweet almond oil, and unrefined hemp seed oil;

(h) reducing the temperature of the homogenous composition obtained in step (g);

(i) heating and stirring the homogenous composition obtained in step (g) to a temperature of about 130'F and then adding one or more essentially paraben and formaldehyde-free preservatives while maintaining heating and stirring for about 40 minutes;

(j) removing heat and stirring the composition produced in step (i) to produce the personal care oil composition.

14. The process for manufacturing a personal care of composition of claim 13 wherein the one or more essentially paraben and formaldehyde-free preservatives in step (i) is phenoxyethanol in a caprylyl glycol emollient base.

15. A method of treating damaged hair in a subject in need thereof comprising applying the composition of claim 1 to the hair and/or scalp of said subject.

16. A method of treating damaged hair in a subject in need thereof by applying the composition of claim 8 to the hair and/or scalp of said subject.

* * * * *